United States Patent [19]

Chin

[11] 4,318,410
[45] Mar. 9, 1982

[54] DOUBLE LUMEN DILATATION CATHETER

[75] Inventor: Albert K. Chin, San Francisco, Calif.

[73] Assignee: Thomas J. Fogarty, Palo Alto, Calif.

[21] Appl. No.: 176,009

[22] Filed: Aug. 7, 1980

[51] Int. Cl.³ .................... A61B 17/00; A61M 29/02
[52] U.S. Cl. ................................ 128/325; 128/344; 128/349 B
[58] Field of Search ............ 128/344, 325, 348, 349.2, 128/349 B, 349 BV, 262, 1 D

[56] References Cited

U.S. PATENT DOCUMENTS

| | | | |
|---|---|---|---|
| 805,851 | 11/1905 | Goldfarb | 128/262 |
| 3,168,092 | 2/1965 | Silverman | 128/262 |
| 3,435,826 | 4/1969 | Fogarty | 128/348 |
| 3,467,101 | 9/1969 | Fogarty et al. | 128/348 |
| 3,467,102 | 9/1969 | Fogarty et al. | 128/348 |
| 3,525,329 | 8/1970 | Zeimer et al. | 128/262 |
| 3,583,391 | 6/1971 | Cox et al. | 128/262 |
| 3,866,599 | 2/1975 | Johnson | 128/6 |
| 3,911,927 | 10/1975 | Fehel et al. | 128/349 B |
| 3,923,065 | 12/1975 | Nozick et al. | 128/348 |
| 4,077,610 | 3/1978 | Masuda | 128/348 |
| 4,085,757 | 4/1978 | Pevsner | 138/344 L |
| 4,109,659 | 8/1978 | Sheriden | 128/262 |
| 4,195,637 | 4/1980 | Grüntzig | 128/349 B X |

*Primary Examiner*—Stephen C. Pellegrino
*Attorney, Agent, or Firm*—Naylor, Neal & Uilkema

[57] ABSTRACT

A dilatation catheter is provided with a balloon element which is invertable, evertable, and inflatable in its everted condition. The catheter is provided with relatively movable members akin to cylinder and piston elements including a port which may be selectively closed off to prevent contrast injection material from being introduced into the blood vessel being treated and opened up for the introduction of contrast injection material into the blood vessel.

5 Claims, 3 Drawing Figures

DOUBLE LUMEN DILATATION CATHETER

RELATED APPLICATION

The subject catheter is an improvement upon the double lumen dilatation catheter constituting the third embodiment of the invention shown and described in the co-pending application of Thomas J. Fogarty and Albert K. Chin for DILATATION CATHETER METHOD AND APPARATUS, Ser. No. 60,408, filed July 25, 1979 now U.S. Pat. No. 4,271,839.

BACKGROUND OF THE INVENTION

The present invention relates to apparatus for use in dilating occluded blood vessels. The invention is particularly concerned with such apparatus wherein dilatation is achieved through the means of a balloon element which is initially inverted within the distal end of a catheter and, in use, extruded through and expanded within the occlusion being treated. The invention is additionally concerned with such apparatus having double lumen characteristics for the catheter to enable the taking of pressure measurements or the making of injections while the catheter remains within the vessel being treated.

SUMMARY OF THE INVENTION

In the improved double lumen catheter of the present invention, the invertable and evertable balloon element is bulbous rather than annular in form and is physically attached only to the outer catheter. The inner catheter is thus made independent of the balloon element in the sense of physical attachment thereto. This means that the distal end of the inner catheter is not within the everted but non-inflated balloon element as the latter is moved for pre-inflation positioning within the occlusion to be treated. Consequently the diameter of the lumen of the inner catheter may be made almost as great as that of the outer catheter. This makes it feasible to efficiently employ the lumen of the inner catheter to inflate the balloon element as well as to inject radiopaque fluid into the vessel. The use of the lumen of the inner catheter for this two-fold purpose in turn enables simplification of the catheter by enabling the incorporation into it of a single syringe port for both balloon inflation and radiopaque fluid injection while enabling the elimination from the catheter of the fluid reservoir which was employed as part of the double lumen catheter of the above-identified patent application.

Other objects, features and advantages of the invention will be apparent from the following description taken in conjunction with the drawing forming part of this specification.

DESCRIPTION OF THE PREFERRED EMBODIMENT

Figures 1, 2, 3:
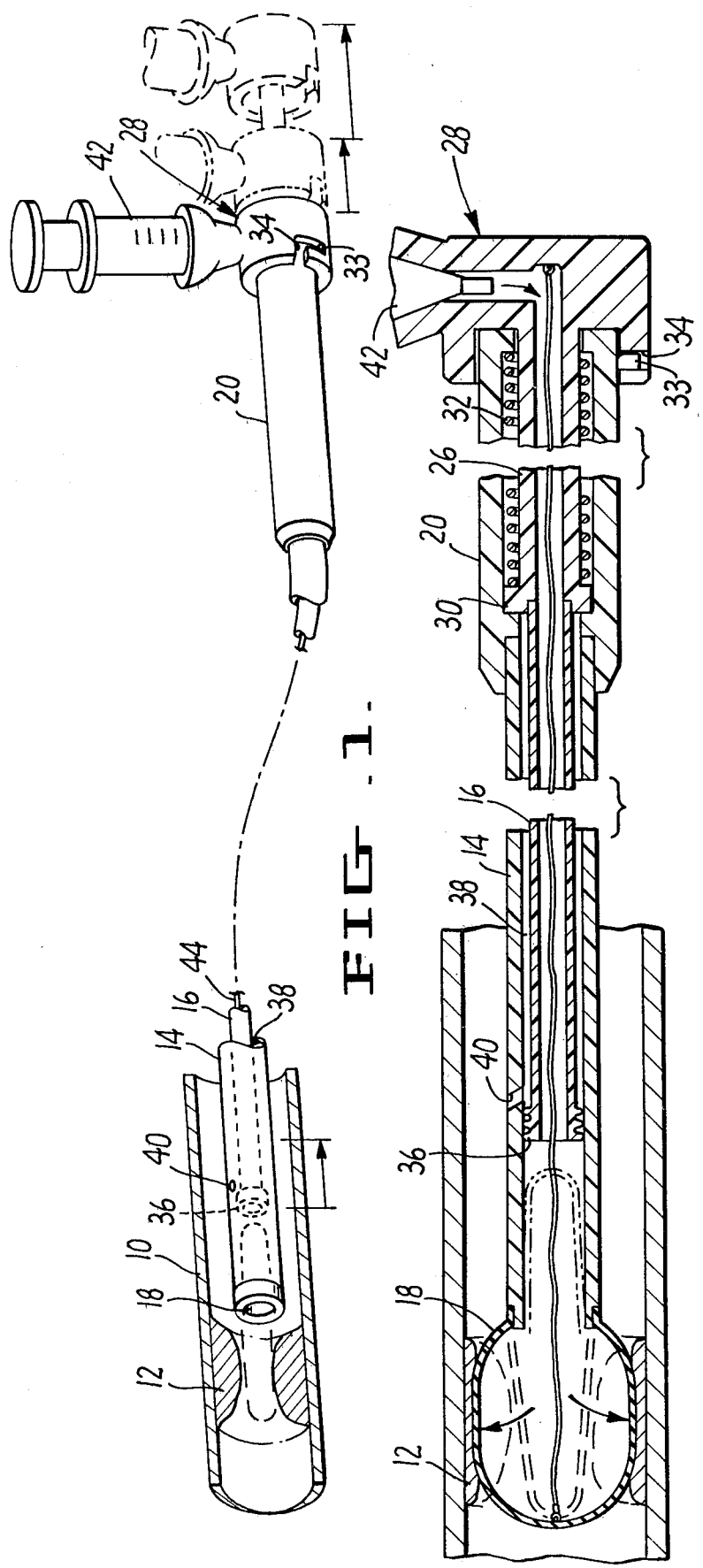
FIG. 1 is a view in perspective illustrating an occluded vessel in the process of being treated by the catheter of the invention.
FIG. 2 is an elevational cross-sectional view illustrating the catheter with the balloon element in inflated condition.
FIG. 3 is a view similar to that of FIG. 2 but showing the catheter with its balloon element in deflated condition and with the inner and outer catheter elements relatively positioned to enable the injection into the vessel of radiopaque material.

FIG. 1 illustrates a blood vessel 10 partially occluded by an occlusion 12. As shown, the vessel is in the form of an artery and the occlusion is what is commonly known as an arteriosclerotic plaque or atheroma. This is the type of adhering occlusion with which the subject catheter has primary application. It should be understood, however, that the invention is usable in treating other types of occluded vessels wherein dilatation is desirable. For example, the catheter of the invention may be used in treating occlusions resulting from fibromuscular dysplasia in veins.

The apparatus comprises a flexible but generally inelastic outer catheter 14, a flexible but generally inelastic inner catheter 16, and a balloon element 18 attached to the distal end of outer catheter 14. As shown in FIG. 2, the balloon element 18 is adapted to have three positional conditions, that is, a normal storage condition in which it is inverted within the end of the outer catheter 14, an everted but non-inflated condition to enable proper emplacement of the balloon element relative to the occlusion, and an inflated condition to dilate the occlusion.

Outer catheter element 14 has its proximal end fixedly attached to sleeve 20 which is provided with lands 22 and 24. Inner catheter 16 has its proximal end fixedly attached to the distal end of a tube 26 forming part of a syringe fitting 28. The tube is provided with a distal flange 30 which is normally adapted to engage land 22 of sleeve 20 under the influence of compression spring 32 which is housed between sleeve 20 and tube 26 and between land 24 and flange 30. Locking means comprising pin 33 carried by sleeve 20 and bayonet slot 34 formed in the fitting 28 are provided to releasably lock sleeve 20 and tube 26 in the condition of FIG. 2 for normal use of the apparatus.

The distal end of inner catheter 16 is provided with a plurality of radially directed sealing ridges 36 which normally prevent the passage of pressurized fluid into the annular space 38 between catheter elements 14 and 16. The outer catheter element 14 is provided with a fluid port 40.

The apparatus is typically used in the following manner. With locking means 33 and 34 mutually engaged and with the balloon element 18 in inverted position within the end of catheter element 14, the catheter device is introduced into the vessel 10 through an appropriate incision, not shown, and moved therealong until its leading end is disposed immediately adjacent the occlusion 12, as shown in FIG. 2. Syringe 42 may then be attached to fitting 28 and operated to fill the interior passageways of elements 14 and 16 of the device and to evert the balloon element 18 to the dotted line position shown in FIG. 2. The subsequent addition of pressurized fluid to the interior of the device with the syringe 42 causes the balloon element 18 to become inflated, as shown in solid outline in FIG. 2, to dilate occlusion 12.

After the occlusion has become compressed to the desired degree the balloon element 18 is deflated to the dotted line everted condition of FIG. 2 for removal of the device from the vessel or for movement of the device to another occlusion to be treated. Alternatively the device may be kept in place with the balloon element in deflated condition for radiopaque fluid injection. This is accomplished by unlocking elements 33 and 34 and by backing the syringe fitting 28 away from sleeve 20 so that the distal end of inner catheter element 16 has been moved sufficiently to uncover port 40. In this condition of the device radiopaque fluid may be introduced through the port into vessel 10.

After the removal of the syringe and the venting of the fluid from the device, the device is restored to its balloon-inverted condition by moving the syringe fitting 28 a sufficient distance away from sleeve 20 to cause cord 44, the ends of which are fixedly attached to fitting 28 and to balloon element 18, to invert the balloon to the inverted dotted line condition of FIG. 2. The syringe fitting 28 may then be re-attached to sleeve 20 by locking means 33 and 34.

The material and relative thicknesses of the balloon element 18 are chosen so that expansion of the balloon element out of the end of the catheter takes place in anisotropic fashion, with the balloon element first everting out of the catheter in advance of substantial lateral expansion and then, after eversion, laterally expanding in response to the continued application of fluid pressure internally of the catheter. Once everted out of the catheter, the balloon element is designed to laterally expand to an outside diameter equal to or greater than the I.D. of the non-occluded vessel being treated. Although such characteristics may be achieved through the employment of an elastomeric balloon element such as that above-described, it is anticipated that similar characteristics may be achieved by fabricating the balloon element of a folded generally inelastic flexible material, such as polyvinyl chloride, which is adapted to first evert to an extended condition and then unfold to a laterally expanded condition.

It is to be pointed out that the subject catheter may be made in the form of single lumen catheter incorporating the usage of a piston which houses a syringe port for balloon inflation and reinversion.

What is claimed is:

1. Apparatus for dilating a partially occluded section of a blood vessel and for introducing a radiopaque fluid into the vessel comprising an elongated flexible catheter, balloon means attached to the distal end of said catheter, a fluid port in said catheter through which radiopaque fluid may be introduced into said vessel, means defining a fluid passageway within said catheter whereby fluid may be introduced into said balloon means, and slide valve means disposed in said catheter and selectively movable relative to said port whereby said port can be brought into communication with said fluid passageway and out of communication therewith.

2. Apparatus for dilating a partially occluded section of a blood vessel and for introducing a radiopaque fluid into the vessel comprising an elongated flexible catheter, balloon means attached to the distal end of said catheter, a fluid port in said catheter, a tubular member slidably disposed in said catheter, said member having an open distal end and having radially directed sealing means carried adjacent said distal end disposed in sealing engagement with the inner surface of said catheter, means associated with said member for introducing fluid into said catheter and into said balloon means through the open distal end of said tubular member, and means for moving said tubular member within said catheter to selectively close off communication between said port and the open distal end of said tubular member and to bring said port and said open distal end into communication with each other.

3. The apparatus of claim 2, said tubular member having an open proximal end attached to a syringe fitting, and means mounting the proximal end of said catheter on said fitting so as to allow limited reciprocal movement of said fitting and tubular member relative to said catheter.

4. The apparatus of claim 3, said mounting means comprising inner and outer annular members, the inner member interconnecting said fitting and said tubular member, the outer member being connected to said catheter, radially projecting flanges on said annular members to maintain said annular members in connected relation while permitting limited sliding movement of one with respect to the other, spring means interengaging said flanges to yieldingly urge said fitting toward said catheter, and complemental locking means to releasably secure said fitting and catheter against movement relative to each other.

5. The apparatus of claim 4, further comprising cord means interconnecting said fitting and the distal end of said balloon means, whereby the movement of said fitting away from said catheter to a first position brings said port and the open distal end of said tubular member into communication with each other without causing said cord means to retract said balloon means and whereby the further movement of said fitting away from said catheter to a second position causes said cord means to retract said balloon means to an inverted position within said catheter.

* * * * *